US006541492B1

(12) United States Patent
Collins et al.

(10) Patent No.: US 6,541,492 B1
(45) Date of Patent: Apr. 1, 2003

(54) THIAZOLE DERIVATIVES AS PPAR GAMMA LIGANDS

(75) Inventors: Jon Loren Collins, Durham, NC (US); Christopher Patrick Holmes, Saratoga, CA (US); James Martin Lenhard, Raleigh, NC (US); Timothy Mark Willson, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/831,672

(22) PCT Filed: Nov. 9, 1999

(86) PCT No.: PCT/EP99/08477

§ 371 (c)(1), (2), (4) Date: May 11, 2001

(87) PCT Pub. No.: WO00/27832

PCT Pub. Date: May 18, 2000

(30) Foreign Application Priority Data

Nov. 8, 1999 (GB) ............................................ 98246143

(51) Int. Cl.⁷ .................... A61K 31/427; A61K 31/426; C07D 274/04; C07D 417/12; C07D 417/06; A61P 19/10
(52) U.S. Cl. .................... 514/342; 514/369; 546/269.7; 548/187; 548/183
(58) Field of Search .................... 546/269.7; 514/342, 514/369; 548/187

(56) References Cited

U.S. PATENT DOCUMENTS 5,994,554 A * 11/1999 Kliewer ...................... 548/183
6,239,157 B1 * 5/2001 Mbalaviele ................. 514/369

FOREIGN PATENT DOCUMENTS

WO WO 99 05161 A 2/1999
WO WO 99 32465 A 7/1999

OTHER PUBLICATIONS

Koromokawa J et al: "3–Substituted 4–oxo–2–thioxo–5–thiazolidineacetic acid", Chemical Abstracts, vol. 074, No. 5, Feb. 01, 1971.
Kinugawa J et al: "2–Thioxo–4–thiazolidinone–5–acetic acid derivatives", Chemical Abstracts vol. 066, No. 3, Jan. 16, 1967.
Ogawa S et al.: "Association of Bone Mineral Denisty with a Polymorphism of the Peroxisome Proliferator–Activated Receptor gamma Gene: PPAR gamma Expression in Osteoblasts", Biochemical and Biophysical Research Communications, vol. 260, No. 1, pp. 122–126.

* cited by examiner

*Primary Examiner*—Evelyn Mei Huang
(74) *Attorney, Agent, or Firm*—Robert H. Brink

(57) ABSTRACT

The present invention discloses novel PPAR gamma ligands of Formula (I) and pharmaceutically acceptable salts and solvates thereof. The present invention also discloses a method for treating osteoporosis by administration of a PPAR gamma antagonist.

9 Claims, No Drawings

THIAZOLE DERIVATIVES AS PPAR GAMMA LIGANDS

This application is filed pursuant to 35 U.S.C. §371 as a United States National Phase Application of International Application No. PCT/EP99/08477 filed Nov. 9, 1999, which claims priority from Great Britain 9824614.3 filed Nov. 11, 1998.

The present invention relates to compounds that bind to and affect PPAR gamma. In another aspect, the present invention relates to methods for prevention or treatment of PPARgamma mediated diseases and conditions and to a method for prevention or treatment of osteoporosis.

Peroxisome Proliferator Activated Receptors (PPARs) are orphan receptors belonging to the steroid/retinoid receptor superfamily of ligand-activated transcription factors. See, for example, Willson, T. M. and Wahli, W., Curr. Opin. Chem. Biol., (1997), Vol. 1, pp 235–241.

Three mammalian PPARs have been identified which are termed PPAR-alpha, PPAR-gamma, and PPAR-delta. PPARs regulate expression of target genes by binding to DNA response elements as heterodimers with the retinoid X receptor. These DNA response elements (PPRE) have been identified in the regulatory regions of a number of genes encoding proteins involved in lipid metabolism and energy balance. The biological role of the PPARs in the regulation of lipid metabolism and storage has been recently reviewed. See, for example, Spiegelman, B. M., Diabetes, (1998), Vol. 47, pp 507–514, Schoonjans, K., Martin, G., Staels, B., and Auwerx, J., Curr. Opin. Lipidol., (1997), Vol. 8, pp 159–166, and Brun, R. P., Kim, J. B., Hu, E., and Spiegelman, B. M., Curr. Opin. Lipidol., (1997), Vol. 8, pp 212–218.

PPAR-gamma ligands of the thiazolidinedione class (TZD) enhance the actions of insulin in man and reduce circulating glucose levels in rodent models of diabetes. The PPAR-gamma receptor is expressed in adipose tissue and plays a pivotal role the regulation of adipocyte differentiation in vitro. TZD such as rosiglitazone induce adipocyte differentiation in vitro through activation of the PPAR-gamma receptor. Thus, although there are clearly therapeutic uses for PPAR-gamma ligands in the treatment of diseases of lipid metabolism and energy balance, it is possible that there will be side effects of these drugs. For example, PPAR-gamma ligands that promote adipocyte differentiation in vivo could lead to increased fat accumulation and weight gain. This side effect might offset the beneficial effects of a PPAR-gamma ligand in the treatment of diabetes or other diseases where obesity is a risk factor. See, for example, the Spiegelman and Brun articles cited above.

Essential dietary fatty acids and certain of their eicosanoid metabolites are naturally occurring hormones for the PPAR-gamma receptor. These hormones can promote adipogenesis through activation of the PPAR-gamma receptor. See, for example, Kliewer, S. A., et al., Proc. Natl. Acad. Sci. USA, (1997), Vol. 94, pp 4318–4323, and Kliewer, S. A., et al., Cell, (1995), Vol. 83, pp 813–819. Molecules that inhibit the adipogenic effects of endogenous PPAR-gamma hormones may be useful in the treatment of diseases caused by increased fat accumulation or lipid storage. See, for example, Tontonoz, P., Hu, E., and Spiegelman, B. M., Curr. Opin. Genet. Dev., (1995), Vol. 5, pp 571–576. Examples of these diseases are obesity, osteoporosis, and acne. For example, it has also been noted that TZD promote adipogenesis in bone marrow and inhibit expression of markers of the osteoblast phenotype such as alkaline phosphatase. See, for example, Paulik, M. A. and Lenhard, J. M., Cell Tissue Res., (1997), Vol. 290, pp 79–87. These effects may lead to low bone mineral density and osteoporosis. Compounds that promote osteogenesis activity may be useful in the treatment of osteoporosis. Similarly, it is known that the TZDs can promote lipid accumulation in sebocytes. See, for example, Rosenfield, R. L., Deplewski, D., Kentsis, A., and Ciletti, N. Dermatology, (1998), Vol. 196, pp 43–46. These effects may lead to sebocyte differentiation and acne formation. Thus, molecules that block adipogenesis in adipocytes, pre-adipocytes, bone marrow, or sebocytes may have beneficial effects in the treatment of obesity, osteoporosis, or acne.

The PPAR-gamma receptor has been found in tissues other than adipose, and it is believed that synthetic PPAR-gamma ligands and natural PPAR-gamma hormones (natural ligands) may have beneficial effects in many other diseases including cardiovascular disease, inflammation, and cancer. See, for example, the Schoonjans article cited above, Ricote, M. et al., Nature, (1998), Vol. 391, pp 79–82, and Mueller, E. et al., Mol. Cell, (1998), Vol. 1, pp 465–470.

There is precedent among other member of the steroid/retinoid receptor superfamily that synthetic ligands can be identified which mimic many of the beneficial effects but inhibit some of the detrimental side effects of the natural hormones. See, for example, McDonnell, D. P., Biochem. Soc. Trans., (1998), Vol. 26, pp 54–60. These synthetic ligands have been given various labels, including antagonists, anti-hormones, partial agonists, selective receptor modulators, tissue selective ligands, and others. See, for example, Katzenellenbogen, J. A., O'Malley, B. W., and Katzenellenbogen, B. S., Mol. Endocinol., (1996), Vol. 10, pp 119–131.

As used herein, a "PPARgamma ligand" is a compound that binds to human PPARgamma with a pKi of greater than 5 when tested in the binding assay described below. As used herein a "PPARgamma antagonist" is a PPARgamma ligand that gives greater than 50% inhibition of lipogenesis when tested in the adipocyte differentiation assay described below and greater than 50% inhibition of transactivation by rosiglitazone when tested in the cell-based reporter assay described below.

Briefly, in one aspect, the present invention discloses compounds of Formula (I) and pharmaceutically acceptable salts and solvates thereof,

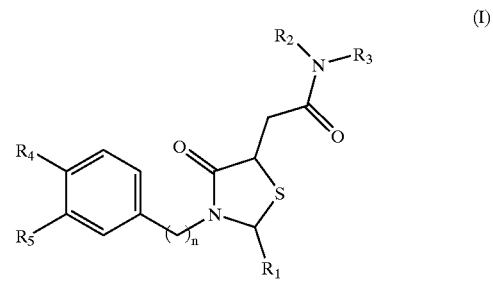

(I)

where n is 2, 3, or 4,

R$_1$ is hexyl, heptyl, or C$_{4-6}$alkyl-phenyl,

R$_2$ is butyl or benzyl optionally substituted with 1 or 2 halogen,

R$_3$ is butyl, benzyl optionally substituted with a trifluoromethyl group or with 1 to 3 halogen, —C$_4$H$_8$OH, p-pyridyl, o-pyridyl, ethylpropionate, propyl, ethyl acetate, o-thiophenmethyl, 2,3-methylenedioxobenzyl, 2-thiazolemethyl, 2-furfuryl, R$_4$ is —COOH, —NHC(O)NH$_2$, —NHS(CH$_3$)O$_2$, —S(NH$_2$)O$_2$), hydantoin, —OH, —OCH$_2$CO$_2$H, —OCH$_2$CONH$_2$, —OCH$_3$, $R_5$ is hydrogen or $R_5$ and $R_4$ are bonded together to form a methylenedioxo ring.

In another aspect, the present invention discloses a method for prevention or treatment of a PPARgamma mediated disease or condition comprising administration of a therapeutically effective amount of a compound of this invention. As used herein, "a compound of the invention" means a compound of formula (I) or a pharmaceutically acceptable salt, or solvates thereof. Particular diseases or conditions are diabetes, obesity, dyslipidemia, metabolic syndrome, osteoporosis, acne, cardiovascular disease, inflammation or cancer.

In another aspect, the present invention provides pharmaceutical compositions comprising a compound of the invention, preferably in association with a pharmaceutically acceptable diluent or carrier.

In another aspect, the present invention discloses a method for prevention or treatment of osteoporosis comprising administration of a therapeutically effective amount of a PPARgamma antagonist.

In another aspect, the present invention provides a compound of the invention for use in therapy, and in particular, in human medicine.

In another aspect, the present invention provides the use of a compound of the invention for the manufacture of a medicament for the treatment of a PPARgamma mediated disease or condition. Particular diseases or conditions are diabetes, obesity, dyslipidemia, metabolic syndrome, osteoporosis, acne, cardiovascular disease, inflammation or cancer.

In another aspect, the present invention provides the use of a PPARgamma antagonist for the manufacture of a medicament for the treatment of osteoporosis.

In another aspect, the present invention provides a method for identifying compounds that will be useful for the treatment of a PPAR gamma mediated disease or condition, comprising the step of binding a compound of this invention to PPAR gamma.

In another aspect, the present invention provides a method for treating a PPAR gamma mediated disease or condition comprising administration of a therapeutically effective amount of a compound that was identified as useful for such treatment by the above method (in other words, by a method comprising the step of binding a compound of this invention to PPAR gamma).

In another aspect, the present invention provides the use of a compound that was identified as useful for treating a PPAR gamma mediated disease or condition by the above method (in other words, by a method comprising the step of binding a compound of this invention to PPAR gamma), for the manufacture of a medicament for the treatment of a PPAR gamma mediated disease or condition.

In another aspect, the invention provides a method for identifying compounds which will be useful in treatment of osteoporosis comprising the step of determining whether a compound antagonises PPAR gamma.

Preferably, when any of the R groups in Formula (I) are alkyl, they are straight chain alkyl.

Preferably, $R_3$ is butyl, benzyl optionally substituted with 1 or 2 halogen, or p-pyridyl.

Suitable compounds of the present invention include:

4-(4-(4-carboxyphenyl)butyl)-2-heptyl4-oxo-5-thiazolidine N,N-dibenzylacetamide, (2S*,5S*)-4-(4-(4-carboxyphenyl)butyl)-2-heptyl-4-oxo-5-thiazolidine N,N-dibenzylacetamide, (2S,5S)-4-(4-(4-carboxyphenyl)butyl)-2-heptyl-4-oxo-5-thiazolidine N,N-dibenzylacetamide, (2S*,5S*)-4-(4-(4-carboxyphenyl)butyl)-2-hexyl-4oxo-5-thiazolidine N,N-dibutylacetamide, (2S*,5S*)-4-(2-(4-carboxyphenyl)ethyl)-2-octyl-4-oxo-5-thiazolidine N,N-dibenzylacetamide, (2R*,5S*)-4-(2-(4-carboxyphenyl)ethyl)-2-octyl-4-oxo-5-thiazolidine N,N-dibenzylacetamide, (2S*,5S*)-4-(2-(4-carboxyphenyl)ethyl)-2-octyl-4-oxo-5-thiazolidine N,N-di-(3-iodo)benzylacetamide, (2S*,5S*)-4-(3-(4-carboxyphenyl)propyl)-2-heptyl-4-oxo-5-thiazolidine N,N-benzylacetamide, (2S*,5S*)-4-(4-(4-carboxyphenyl)butyl)-2-heptyl-4-oxo-5-thiazolidine N,N-di-(3-benzylacetamide, (2S*,5S*)-4-(2-(4-carboxyphenyl)ethyl)-2-(6-phenylhexyl)-4-oxo-5-thiazolidine N,N-dibenzylacetamide, (2S*,5S*)-4-(4-(4-carboxyphenyl)butyl)-2-(6-phenylhexyl)-4-oxo-5-thiazolidine N,N-dibenzylacetamide, 4-(4-(4-carboxyphenyl)butyl)-2-(4-phenylbutyl)-4-oxo-5-thiazolidine N,N-dibenzylacetamide, (2S*,5S*)-4-(2-(4-ureidophenyl)ethyl)-2-octyl-4-oxo-5-thiazolidine N,N-dibenzylacetamide, (2S,5S*)-4-(2-(4-methylsufonamidophenyl)ethyl)-2-octyl-4-oxo-5-thiazolidine N,N-dibenzylacetamide, (2S*,5S*)-4-(2-(4-aminosulfonylphenyl)ethyl)-2-octyl-4-oxo-5-thiazolidine N,N-dibenzylacetamide, (2S*,5S*)-4-(4-(4-carboxyphenyl)butyl)-2-heptyl-4-oxo-5-thiazolidine N-benzyl-N-(4-trifluorobenzyl)acetamide, (2R*,5S*)-4-(4-(4-carboxyphenyl)butyl)-2-heptyl-4-oxo-5-thiazolidine N-benzyl-N-4-trifluorobenzyl)acetamide, (2S*,5S*)-4-(2-(4-(3-hydantoino)phenyl)ethyl)-2-octyl-4-oxo-5-thiazolidine N,N-dibenzylacetamide, (2S*,5S*)-4-(2-(3,4-dioxomethylenephenyl)ethyl)-2-heptyl-4-oxo-5-thiazolidine N,N-dibenzylacetamide, (2S*,5S*)-4-(4-(4-carboxyphenyl)butyl)-2-octyl-4-oxo-5-thiazolidine N-benzyl-N-(4-hydroxybutyl)acetamide, (2S*,5S*)-4-(2-(3,4-dioxomethylenephenyl)ethyl)-2-octyl-4-oxo-5-thiazolidine N,N-dibenzylacetamide, (2S*,5S*)-4-(4-(4-carboxyphenyl)butyl)-2-heptyl-4-oxo-5-thiazolidine N-benzyl-N-(4-pyridyl)acetamide, (2S*,5S*)-4-(4-(4-carboxyphenyl)butyl)-2-heptyl-4-oxo-5-thiazolidine N-benzyl-N-(2-pyridyl)acetamide, (2S*,5S*)-4-(4-(4-carboxyphenyl)butyl)-2-heptyl-4-oxo-5-thiazolidine N-benzyl-N-(2-ethoxycarboxyethyl)acetamide, (2S*,5S*)-4-(4-(4-(carboxyphenyl)butyl)-2-heptyl-4-oxo-5-thiazolidine N-benzyl-N-butylacetamide, (2S*,5S*)-4-(4-(4-carboxyphenyl)butyl)-2-heptyl-4-oxo-5-thiazolidine N-benzyl-N-isopropylacetamide, (2S*,5S*)-4-(2-(4-hydroxyphenyl)ethyl)-2-heptyl-4-oxo-5-thiazolidine N,N-dibenzylacetamide, (2S*,5S*)-4-(4-(4-carboxyphenyl)butyl)-2-heptyl-4-oxo-5-thiazolidine N-benzyl-N-ethoxycarboxymethylacetamide, (2S*,5S*)-4-(4-(4-carboxyphenyl)butyl)-2-heptyl-4-oxo-5-thiazolidine N,N-di-(4-fluorobenzyl)acetamide, (2S*,5S*)-4-(2-(4-carboxymethoxyphenyl)ethyl)-2-heptyl-4-oxo-5-thiazolidine N,N-dibenzylacetamide, (2S*,5S*)-4-(2-(4-carboxyamidomethoxyphenyl)ethyl)-2-heptyl-4-oxo-5-thiazolidine N,N-dibenzylacetamide, (2S*,5S*)-4-(2-(4-methoxyphenyl)ethyl)-2-heptyl-4-oxo-5-thiazolidine N,N-dibenzylacetamide, (2S*,5S*)-4-(4-(4-carboxyphenyl)butyl)-2-heptyl-4-oxo-5-thiazolidine N-benzyl-N-(2-thienylmethyl)acetamide, (2S*,5S*)-4-(4-(4-carboxyphenyl)butyl)-2-heptyl-4-oxo-5-thiazolidine N-benzyl-N-(2,3-dioxomethylenebenzyl)acetamide, (2S*,5S*)-4-(4-(4-carboxyphenyl)butyl)-2-heptyl-4-oxo-5-thiazolidine N-benzyl-N-(2-thiazolemethyl)acetamide, (2S*,5S*)-4-(4-(4-carboxyphenyl)butyl)-2-heptyl-4-oxo-5-thiazolidine N-benzyl-N-(2-furfuryl)acetamide, and pharmaceutically acceptable salts and solvates thereof.

Particularly preferred compounds of the present invention include:

(2S*,5S*)-4-(4-(4-carboxyphenyl)butyl)-2-heptyl-4-oxo-5-thiazolidine N,N-dibenzylacetamide, (2S,5S)-4-(4-(4-carboxyphenyl)butyl)-2-heptyl-4-oxo-5-thiazolidine N,N-dibenzylacetamide, (2S*,5S*)-4-(4-(4-carboxyphenyl)butyl)-2-hexyl-4-oxo-5-thiazolidine N,N-dibutylacetamide, (2S*,5S*)-4-(4-(4-carboxyphenyl)butyl)-2-octyl-4-oxo-5-thiazolidine N-benzyl-N-(4-hydroxybutyl)acetamide, (2S*,5S*)-4-(4-(4-carboxyphenyl)butyl)-2-heptyl-4-oxo-5-thiazolidine N-benzyl-N-(4-pyridyl)acetamide, (2S*,5S*)-4-(4-(4-carboxyphenyl)butyl)-2-heptyl-4-oxo-5-thiazolidine N-benzyl-N-(2-thiazolemethyl)acetamide, and pharmaceutically acceptable salts and solvates thereof.

Those skilled in the art will recognise that stereocenters exist in compounds of Formula (I). Accordingly, the present invention includes all possible stereoisomers and geometric isomers of formula (I) and includes not only racemic compounds but also the optically active isomers as well. When a compound of formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Additionally, in situations where tautomers of the compounds of formula (I) are possible, the present invention is intended to include all tautomeric forms of the compounds.

While the compounds of this invention include all enantiomers and diastereomers, the trans pair of diastereomers is preferred. This pair consists of the (2S, 5S) enantiomer and the (2R, 5R) enantiomer. This diastereomer pair will be abbreviated as (2S*,5S*). Most preferred are the (2S,5S) enantiomers.

It will also be appreciated by those skilled in the art that the compounds of the present invention may also be utilised in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of Formula (I) and their pharmaceutically acceptable salts and solvates.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day.

While it is possible that compounds of the present invention may be therapeutically administered as the raw chemical, it is preferable to present the active ingredient as a pharmaceutical formulation. Accordingly, the present invention further provides for a pharmaceutical formulation comprising a compound of Formula (I) or a pharmaceutically acceptable salt or solvate thereof, preferably together with one or more pharmaceutically acceptable carriers therefor and, optionally, other therapeutic and/or prophylactic ingredients.

Formulations of the present invention include those especially formulated for oral, buccal, parenteral, transdermal, inhalation, intranasal, transmucosal, implant, or rectal administration, however, oral administration is preferred. For buccal administration, the formulation may take the form of tablets or lozenges formulated in conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. The tablets may be coated according to methods well known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides. Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle (e.g., sterile, pyrogen-free water) before use.

The formulations according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (as an emulsion in an acceptable oil, for example), ion exchange resins or as sparingly soluble derivatives as a sparingly soluble salt, for example.

The formulations according to the invention may contain between 0.1–99% of the active ingredient, conveniently from 30–95% for tablets and capsules and 3–50% for liquid preparations.

The novel thiazolidine acetamides of this invention can be used to inhibit adipogenesis. Surprisingly, it has been found that PPARgamma ligands that inhibit adipogenesis also stimulate alkaline phosphatase activity, which is a surrogate marker for stimulation of osteogenesis. In addition to this activity, these novel PPAR-gamma ligands maintain many of the beneficial effects of known PPAR-gamma ligands, such as antidiabetic activity.

Thus, synthetic PPAR-gamma ligands that block adipogenesis while mimicking the beneficial effects of natural PPAR-gamma hormones will be useful for the treatment of human disease, including diabetes, obesity, dyslipidemia, metabolic syndrome, osteoporosis, acne, cardiovascular disease, inflammation, or cancer.

The compounds of this invention can be prepared by standard organic chemistry as illustrated by the accompanying working examples. The following examples are set forth to illustrate the synthesis of some particular compounds of the present invention and to exemplify general processes. Accordingly, the following Examples section is in no way intended to limit the scope of the invention contemplated herein.

EXAMPLES

As used herein the symbols and conventions used in these processes, schemes and examples are consistent with those used in the contemporary scientific literature, for example, the Journal of the American Chemical Society. Unless otherwise noted, all starting materials were obtained from commercial suppliers and used without further purification. Specifically, the following abbreviations may be used in the examples and throughout the specification: g (grams); mg (milligrams); L (liters); mL (milliliters); µL (microliters); N (normal); mM (millimolar); mmol (millimoles); i.v. (intravenous); Hz (Hertz); MHz (megahertz); mol (moles); RT or rt (room temperature); min (minutes); h (hours); mp. (melting point); TLC (thin layer chromatography); HPLC (high pressure liquid chromatography); ms (mass spectrum); ES+ (electrospray); $R_f$ (retention fraction); ($t_r$ (retention time); RP (reverse phase); MeOH (methanol); TFA (trifluoroacetic acid); HCl (hydrochloric acid); $HCO_2H$ (formic acid); THF (tetrahydrofuran); $CH_3CN$ (acetonitrile); EtOH (ethanol); $CDCl_3$ (deuterated chloroform); DMSO (dimethylsulfoxide); DMSO-$d_6$ (dimethylsulfoxide-deuterated); EtOAc (ethyl acetate); DCM or $CH_2Cl_2$ (dichloromethane); DMF (dimethylformamide); $Et_3N$ (triethylamine); $MgSO_4$ (magnesium sulfate); $H_2O$ (water); LAH (lithium aluminum hydride; NaH (sodium hydride); $Na_2CO_3$ (sodium carbonate); $Na_2SO_4$ (sodium sulfate); $MnO_2$ (manganese dioxide); NaOH (sodium hydroxide; LiOH (lithium hydroxide); DIEA (diisopropylethylamine); $Et_2O$ (diethyl ether; diethyl azodicaboxylate (DEAD); tert-butyloxycarbonyl (BOC); $NaHCO_3$ (saturated aqueous sodium bicarbonate). Brine refers to a saturated aqueous solution of NaCl. Unless otherwise indicated, all temperatures are expressed in ° C. (degrees Centigrade). All reactions conducted at room temperature unless otherwise noted.

The $^1H$ NMR spectra were recorded on a Varian VXR-300, a Varian Unity-300, or a Varian Unity-400 instrument. Chemical shifts are expressed in parts per million (ppm, δ units). Coupling constants are in units of hertz (Hz). Splitting patterns are designated as s, singlet; d, doublet; t, triplet; q, quartet; m, multiplet; br, broad; hept, heptuplet.

Low-resolution mass spectra (MS) were recorded on a JOEL JMS-AX505HA, JOEL SX-102 or a SCIEX-APIiii spectrometers. All mass spectra were taken under electro-spray ionization (ES, either in the positive ion mode or negative ion mode) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, iodine staining, or 7% ethanolic phosphomolybdic acid or p-anisldehyde solutions. Flash column chromatography was performed on silica gel (230–400 mesh, Merck).

Analytical purity was assessed on a Hewlett Packard series 1050 or 1100 system equipped with a diode array spectrometer. The stationary phase was either a Dynamax C8 column (25 cm×4.1 mm), a Dynamax 60A C18 column (25 cm×4.6 mm), a Vydac C18 column (5m, 4.6 mm×250 mm), a Supelco C18 column (5 m, 4.6 mm×150 mm), or a Rainin C18 column (5 m, 4.6 mm×250 mm). The flow rate was 1.0 to 1.5 ml/min. (t0=2.8 or 3.0 min.) and the solvent systems were as described below. Enantiomeric purity was assessed using either a Chiralpak AD column (25 cm×4.6 mm) or a Chiralpak OD column (25cm×4.6 mm) on either a Hewlet Packard series 1050 HPLC system equipped with a diode array spectrometer or on a Supercritical Fluid (SFC) system using $CO_2$/methanol as the mobile phase.

Example 1

4-(4-(4-Carboxyphenyl)butyl)-2-heptyl-4-oxo-5-thiazolidine N,N-Dibenzylacetamide 9-Fluorenylmethyl chloroformate (6.9 g) was added to biphasic mixture of tert-butyl 4-(4-aminobutyl)benzoate (5.7 g) in THF (100 mL) and saturated aqueous $NaHCO_3$ (50 mL). The resulting mixture was stirred at r.t. for 1 h and then diluted with EtOAc and $H_2O$. The organic layer was separated and washed with brine, dried over $MgSO_4$, filtered and concentrated. The crude material was purified by flash chromatography to give 7.4 g of tert-butyl 4-(4-(9-fluorenylmethoxycarbonyl)-aminobutyl)benzoate.

Trifluoroacetic acid (100 mL) was added to a solution of tert-butyl 4-(4-(9-fluorenylmethoxycarbonyl)aminobutyl) benzoate (6.9 g) in $CH_2Cl_2$. The resulting solution was stirred at rt. for 3 h and then concentrated. The crude product was triturated with hexane and the solid collected by filtration to give 5.5 g of 4-(4-(9-fluorenylmethoxycarbonyl) amino)butylbenzoic acid.

A mixture of 4-(4-(9-fluorenylmethoxycarbonyl)amino) butylbenzoic acid (2.8 g) in $CH_2Cl_2$ (30 mL) was treated with 2-fluoro-1,3-dimethylpyridinium tosylate (2.1 g) followed by N,N-diisopropylethylamine (3.7 mL). The solution was shaken for 15 min, and then Sasrin resin (4 g, 0.89 mmol/g) was added followed by 4-dimethylaminopyridine (0.1 g). The mixture was shaken for 5 h and then drained. The resin was washed with DMF, $CH_2Cl_2$, MeOH and $Et_2O$. The resulting resin was treated with 0.5 M acetic anhydride in $CH_2Cl_2$ (20 mL) and 0.5 M pyridine in $CH_2Cl_2$ (20 mL) and shaken for 30 min and then drained. The resin was washed with DMF, $CH_2Cl_2$, MeOH and $Et_2O$. FMOC analysis showed a loading of 0.5 mmol/g.

A solution of 20% piperidine in DMF (8 mL) was added a reaction vessel containing an aliquot of the resin (0.5 g). The mixture was shaken for 45 min and then drained and washed with DMF, $CH_2Cl_2$, MeOH, $Et_2O$ and THF. The resin was transferred to a 40 mL glass scintillation vial with a Teflon lined cap. A THF solution (15 mL) of octanal (0.75 M) and mercaptosuccinic acid (2 M) was added followed by activated 3 Å sieves (100 mg). The mixture was heated at 70° C. with shaking for 4 h. The resin was drained and washed with DMF, $CH_2Cl_2$, MeOH and $Et_2O$. An aliquot of the resulting resin (50 mg) was treated with a solution of pentafluorophenyl trifluoroacetate (0.09 mL) and pyridine (0.09 mL) in DMF (0.18 mL) and shaken for 4 h. The resin was drained and washed with DMF. A DMF solution (0.75 mL) of N,N-dibenzylamine (0.5 M), N,N-diisopropylethylamine (0.6 M) and 4dimethylaminopyridine (0.01 M) was added. The mixture was shaken at rt. for 18 h. The resin was drained and washed with DMF, $CH_2Cl_2$, MeOH and $Et_2O$. The resin was cleaved with 10% TFA in $CH_2Cl_2$ (0.25 mL) for 30 min. The resulting solution was collected and the resin washed with $CH_2Cl_2$. The combined $CH_2Cl_2$ solutions were concentrated to yield 7 mg of 4-(4-(4-carboxyphenyl)butyl)-2-heptyl-4-oxo-5-thiazolidine N,N-dibenzylacetamide as a mixture of cis:trans (2S*, 5R*:2S*,5S*) isomers: MS (ES+) 601. The isomers could be separated by C18 reverse phase HPLC.

Example 2

(2S*,5S*)-4-(4-(4-Carboxyphenyl)butyl)-2-heptyl-4-oxo-5-thiazolidine N,N-Dibenzylacetamide In a sealed tube tert-butyl 4-iodobenzoate (28.1 g) was dissolved in trethylamine (26 mL). N-phthalyl-3-butene (19.5 g), palladium (II) acetate (1.0 g) and tri-o-tolylphosphine (2.8 g) were added. Nitrogen was bubbled through the reaction for 10 min and then the reaction vessel was sealed. The reaction was placed in an oil bath preheated to 110° C. and stirred for 4.5 h. The reaction was cooled to r.t. Ethyl acetate (250 mL) and 1N HCl (100 mL) were added and the reaction stirred until solids were dissolved. The mixture was filtered through a plug of celite and then the layers separated. The aqueous fraction was extracted with ethyl acetate (3×50 mL) and the combined organic extracts were dried over $MgSO_4$, filtered and concentrated. The solids were triturated with hexane and the solids filtered and collected to afford 11.8 g of tert-butyl 4-[(E)-4-(1,3-dioxo-1,3-dihydro-2H-isoindol-2-yl)-1-butenyl]benzoate: 1H NMR ($CDCl_3$, 400 MHz) 7.88 (d, 2H, J=8.4 Hz), 7.82 (dd, 2H, J=3.1, 3.1 Hz), 7.77 (dd, 2H J=3.0, 3.1 Hz), 7.32 (d, 2H, J=8.2 Hz), 6.45 (d, 1H, J=15.9 Hz), 6.28 (dt, 1H, J=7.2, 15.9, 7.2 Hz), 3.85 (t, 2h, J=7.0 Hz), 2.65 (q, 2H, J=6.9 Hz), 1.60 (s, 9H).

tert-Butyl 4-[(E)-4-(1,3-dioxo-1,3-dihydro-2H-isoindol-2-yl)-1-butenyl]benzoate (15.1 g) was dissolved in 1:1 THF/ EtOH (150 mL). 10% Pd on carbon (6.0 g) was added and the reaction placed on a Parr hydrogenator under 50 psi of $H_2$. The reaction was shaken for 6 h. The reaction was filtered through a pad of celite and the celite washed with ethanol (3×100 mL). The organic extracts were concentrated to afford 15.3 g of tert-butyl 4-[4-(1,3-dioxo-1,3-dihydro-2H-isoindol-2-yl)butyl]benzoate: 1H NMR ($CDCl_3$, 400 MHz) 7.88 (d, 2H, J=8.1 Hz), 7.82 (dd, 2H, J=3.0, 3.1 Hz), 7.77 (dd, 2H, J=3.0, 3.2 Hz), 7.2 (d, 2H, J=8.1 Hz), 3.7 (t, 2 h, J=6.9 Hz), 2.7 (t, 2H, J=6.9 Hz), 1.7 (m, 4H), 1.60 (s, 9H).

To tert-butyl 4-[4-(1,3-dioxo-1,3-dihydro-2H-isoindol-2-yl)butyl]benzoate (33.2 g) in ethanol (600 mL) was added hydrazine (16.9 g). The reaction was heated to reflux and stirred for 2 h. The reaction was then cooled to r.t. and filtered. The solids were washed with ethanol (4×200 mL). The combined organic extracts were concentrated and then dissolved in $CH_2Cl_2$ and insoluble material removed by filtration. The organic extracts were concentrated to afford 17.1 g of tert-butyl 4-(4-aminobutyl)benzoate: 1H NMR ($CDCl_3$, 400 MHz) 7.90 (d, 2H, J=8.2 Hz), 7.2 (d, 2H, J=8.0 Hz), 2.7 (m, 2H,), 1.7 (m, 4H), 1.60 (s, 9H), 1.4 (m, 2H).

tert-Butyl 4-(4-aminobutyl)benzoate (8.1 g), mercaptosuccinic acid (10.3 g) and octanal (8.4 g) in toluene (320 mL) were heated to reflux for 18 h. The reaction was cooled to r.t. and diluted with ethyl acetate (300 mL). The organic extracts were washed with water (3×300 mL), brine (300 mL), dried over $MgSO_4$, filtered and concentrated to afford 28.5 g of a golden oil. The oil was dissolved in $CH_2Cl_2$ (250 mL) and cooled to 0° C. HOBT (5.5 g) and EDC (7.8 g) were added and the reaction stirred for 30 min. Dibenzylamine (8.1 g) was added and the reaction stirred for 2 d. The resulting mixture was washed with water (500 mL), brine (500 mL), dried over $MgSO_4$, filtered and concentrated. The crude material was purified and the cis:trans isomers separated by flash chromatography to afford 4.3 g of (2S*,5S*)-4-(4-(4-tert-butylcarboxyphenyl)butyl)-2-heptyl-4-oxo-5-thiazolidine N,N-dibenzylacetamide, 4.8 g of (2R*,5S*)-4-(4-(4-tert-butylcarboxyphenyl)butyl)-2-heptyl-4-oxo-5-thiazolidine N,N-dibenzylacetamide, and 5.86 g of the cis:trans mixture: 1H NMR ($CDCl_3$, 400 MHz) trans isomer 7.88 (d, 2H, J=8.0 Hz), 7.38–7.26 (m, 6H), 7.22–7.12 (m, 6H), 4.74 (d, 1H, J=14.7 Hz), 4.52–4.30 (m, 4H), 3.72–3.62 (m, 1H), 3.47 (dd, 1H, J=3.0, 13.7 Hz), 3.04–2.95 (m, 1H), 2.78–2.60 (m, 3H), 1.62–1.55 (m, 14H), 1.31–1.25 (m, 8H), 0.88 (t, 3H, J=6.8 Hz).

(2S*,5S*)-4-(4-(4-tert-butylcarboxyphenyl)butyl)-2-heptyl-4-oxo-5-thiazolidine N,N-dibenzylacetamide (13.3 g) was dissolved in a 1:1 solution of TFA/$CH_2Cl_2$ and stirred at r.t. for 2 h. The reaction was concentrated and azetroped with $CH_2Cl_2$ (3×200 mL) and ether (3×200 mL). The residue was dissolved in ether (15 mL) and hexane (200 mL). The solution was stirred overnight and filtered to afford 9.2 g of (2S*,5S*)-4-(4-(4-carboxyphenyl)butyl)-2-heptyl-4-oxo-5-thiazolidine N,N-dibenzylacetamide as a white solid: m.p. 94–97° C.; 1H NMR ($CDCl_3$, 400 MHz 7.96 (d, 2H, J=8.2 Hz), 7.40–7.20 (m, 10H), 7.14 (d, 2H, J=7.2 Hz), 4.74 (d, 1H, J=14.7 Hz), 4.54–4.28 (m, 5H), 3.72–3.62 (m, 1H), 3.47 (dd, 1H, J=3.0, 13.8 Hz), 3.04–2.95 (m, 1H), 2.78–2.60 (m, 3H), 1.90–1.80 (m, 1H), 1.70–1.50 (m, 8H), 1.44–1.3 m, 8H), 0.88 (t, 3H, J=6.8 Hz); Anal. ($C_{37}H_{46}N_2S_1O_4$) C, 72.31; H, 7.49; N, 4.56; S, 5.21 Found C, 72.24; H, 7.54; N, 4.56; S, 5.16.

Example 3
(2S,5S)-4-(4-(4-Carboxyphenyl)butyl)-2-heptyl-4-oxo-5-thiazolidine N,N-Dibenzylacetamide (2S*,5S*)-4-(4-(4-carboxyphenyl)butyl)-2-heptyl-4-oxo-5-thiazolidine N,N-dibenzylacetamide was a resolved by chiral HPLC using a Daicel AD column (2×25 cm) with 15% isopropanol/hexane as the mobile phase at a flow rate of 8 mL/min. Monitoring at 230 nM, peak 1 was observed at 220 min and peak 2 was observed at 260 min. Peak 1 was collected and concentrated to give (2S,5S)-4-(4-(4-carboxyphenyl)butyl)-2-heptyl-4-oxo-5-thiazolidine N,N-dibenzylacetamide. Absolute stereochemistry was assigned by X-ray crystallography. Peak 2 was collected and concentrated to give (2R,5R)-4-(4-(4-carboxyphenyl)butyl)-2-heptyl-4-oxo-5-thiazolidine N,N-dibenzylacetamide.

Examples 4–36
In a similar manner to the preparation of Examples 1–3, the following examples were prepared.

Example 4
(2S*,5S*)-4-(4-(4-Carboxyphenyl)butyl)-2-hexyl-4-oxo-5-thiazolidine N,N-Dibutylacetamide

Example 5
(2S*,5S*)-4-(2-(4-Carboxyphenyl)ethyl)-2-octyl-4-oxo-5-thiazolidine N,N-Dibenzylacetamide

Example 6
(2R*,5S*)-4-(2-(4-Carboxyphenyl)ethyl)-2-octyl-4-oxo-5-thiazolidine N,N-Dibenzylacetamide

Example 7
(2S*,5S*)-4-(2-(4-Carboxyphenyl)ethyl)-2-octyl-4-oxo-5-thiazolidine N,N-Di-(3-iodo)benzylacetamide

Example 8
(2S*,5S*)-4-(3-(4-Carboxyphenyl)propyl)-2-heptyl-4-oxo-5-thiazolidine N,N-Benzylacetamide

Example 9
(2S*,5S*)-4-(4-(4-Carboxyphenyl)butyl)-2-heptyl-4-oxo-5-thiazolidine N,N-Di-(3-benzylacetamide

Example 10
(2S*,5S*)-4-(2-(4-Carboxyphenyl)ethyl)-2-(6-phenylhexyl-4-oxo-5-thiazolidine N,N-Dibenzylacetamide

Example 11
(2S*,5S*)-4-(4-(4-Carboxyphenyl)butyl)-2-(6-phenylhexyl)-4-oxo-5-thiazolidine N,N-Dibenzylacetamide

Example 12
4-(4-(4-carboxyphenyl)butyl)-2-(4-phenylbutyl)-4-oxo-5-thiazolidine N,N-Dibenzylacetamide

Example 13
(2S*,5S*)-4-(2-(4-Ureidophenyl)ethyl)-2-octyl-4-oxo-5-thiazolidine N,N-Dibenzylacetamide

Example 14
(2S*,5S*4-(2-(4-Methylsulfonamidophenyl)ethyl)-2-octyl-4-oxo-5-thiazolidine N,N-Dibenzylacetamide

Example 15
(2S*,5S*4-(2-(4-Aminosulfonylphenyl)ethyl)-2-octyl-4-oxo-5-thiazolidine N,N-Dibenzylacetamide

Example 16
(2S*,5S*)-4-(4-(4-Carboxyphenyl)butyl)-2-heptyl-4-oxo-5-thiazolidine N-Benzyl-N-(4-trifluorobenzyl)acetamide

Example 17
(2R*,5S*)-4-(4-(4-Carboxyphenyl)butyl)-2-heptyl-4-oxo-5-thiazolidine N-Benzyl-N-(4-trifluorobenzyl)acetamide

Example 18
(2S*,5S*)-4-(2-(4-(3-Hydantoino)phenyl)ethyl)-2-octyl-4-oxo-5-thiazolidine N,N-Dibenzylacetamide

Example 19
(2S*,5S*)-4-(2-(3,4-Dioxomethylenephenyl)ethyl)-2-heptyl-4-oxo-5-thiazolidine N,N-Dibenzylacetamide

Example 20
(2S*,5S*)-4-(4-(4-Carboxyphenyl)butyl)-2-octyl-4-oxo-5-thiazolidine N-Benzyl-N-(4-hydroxybutyl)acetamide

Example 21
(2S*,5S*)-4-(2-(3,4-Dioxomethylenephenyl)ethyl)-2-octyl-4-oxo-5-thiazolidine N,N-Dibenzylacetamide

Example 22
(2S*,5S*)-4-(4-(4-Carboxyphenyl)butyl)-2-heptyl-4-oxo-5-thiazolidine N-Benzyl-N-(4-pyridyl)acetamide

Example 23
(2S*,5S*)-4-(4-(4-Carboxyphenyl)butyl)-2-heptyl-4-oxo-5-thiazolidine N-Benzyl-N-(2-pyridyl)acetamide

Example 24
(2S*,5S*)-4-(4-(4-Carboxyphenyl)butyl)-2-heptyl-4-oxo-5-thiazolidine N-Benzyl-N-(2-ethoxycarboxyethyl)acetamide

Example 25
(2S*,5S*)-4-(4-(4-Carboxyphenyl)butyl)-2-heptyl-4-oxo-5-thiazolidine N-Benzyl-N-butylacetamide

Example 26
(2S*,5S*)-4-(4-(4-Carboxyphenyl)butyl)-2-heptyl-4-oxo-5-thiazolidine N-Benzyl-N-isopropylacetamide

Example 27
(2S*,5S*)-4-(2-(4-Hydroxyphenyl)ethyl)-2-heptyl-4-oxo-5-thiazolidine N,N-Dibenzylacetamide

Example 28
(2S*,5S*)-4-(4-(4-Carboxyphenyl)butyl)-2-heptyl-4-oxo-5-thiazolidine N-Benzyl-N-ethoxycarboxymethylacetamide

Example 29
(2S*,5S*)-4-(4-(4-Carboxyphenyl)butyl)-2-heptyl-4-oxo-5-thiazolidine N,N-Di-(4-fluorobenzyl)acetamide

Example 30
(2S*,5S*)-4-(2-(4-Carboxymethoxyphenyl)ethyl)-2-heptyl-4-oxo-5-thiazolidine N,N-Dibenzylacetamide

Example 31
(2S*,5S*)-4-(2-(4-Carboxyamidomethoxyphenyl)ethyl)-2-heptyl-4-oxo-5-thiazolidine N,N-Dibenzylacetamide

Example 32
(2S*,5S*)-4-(2-(4-Methoxyphenyl)ethyl)-2-heptyl-4-oxo-5-thiazolidine N,N-Dibenzylacetamide

Example 33
(2S*,5S*)-4-(4-(4-Carboxyphenyl)butyl)-2-heptyl-4-oxo-5-thiazolidine N-Benzyl-N-(2-thienylmethyl)acetamide

Example 34
(2S*,5S*)-4-(4-(4-Carboxyphenyl)butyl)-2-heptyl-4-oxo-5-thiazolidine N-Benzyl-N-(2,3-dioxomethylenebenzyl)acetamide

Example 35
(2S*,5S*)-4-(4-(4-Carboxyphenyl)butyl)-2-heptyl-4-oxo-5-thiazolidine N-Benzyl-N-(2-thiazolemethyl)acetamide

Example 36

(2S*,5S*)-4-(4-(4-Carboxyphenyl)butyl)-2-heptyl-4-oxo-5-thiazolidine N-Benzyl-N-(2-furfuryl) acetamide Binding Assay Test compounds were assayed for binding to the human PPAR-gamma receptor ligand binding domain as described in Nichols, J. S., Parks, D. J., Consler, T. G., and Blanchard, S. G., Anal. Biochem., (1998), Vol. 257, pp 112–119. Each of the above Examples 1–36 had a $pK_i>5$ in this binding assay.

Cell-based Reporter Assay

CV-1 cells were maintained in DME High Glucose medium (Irvine Scientific) supplemented with 10% fetal bovine serum and 2 mM Glutamine. Cells were split into D-MEM/F-12 medium (Gibco) supplemented with 10% charcoal stripped fetal bovine serum for 3 d before harvesting. Cells were harvested into D-MEM/F-12 medium (Gibco) supplemented with 10% charcoal stripped fetal bovine serum and counted. Cells were seeded at a density of 24,000 cells per well into 96-well plates and incubated overnight at 5% $CO_2$ and 37° C. Cells were transfected for 6 to 20 hours based on the Lipofectamine protocol (Gibco) with the following amounts of DNA per well: 2 ng PSG5 GAL4-human PPAR-gamma, 8 ng UAS-tk-SPAP, 25 ng beta-gal, 45 ng pBluescript. See Lehmann, J. M. et al., J. Biol. Chem., (1995), Vol. 270, pp 12953–12956 and Brown, P. J. et al., Chem. Biol., (1997), Vol. 4, pp 909–918. Cells were incubated overnight at 5% $CO_2$ and 37° C. Test compounds were solublized to 10 mM in DMSO. Test compounds were then serially diluted from 1e-5 M to 1e-10 M into D-MEM/F-12 (Gibco) medium supplemented with 10% delipidated and charcoal stripped calf serum (Sigma) heat inactivated at 60° C. for 30 minutes, 2 mM Glutamine, and Pen-Strep. This medium into which the test compounds were diluted also contained 100 nM rosiglitazone. These test compound dilutions were added 100 microliters/well to the transfected cell plates after the transfection media were aspirated. DMSO controls and 1 micromolar rosiglitazone controls were added to each cell plate. Cells were incubated overnight at 5% $CO_2$ and 37° C. Cells were lysed with 25 microliters 0.5% Triton X-100. Two daughter plates were made from each mother plate. One daughter received 200 microliters/well SPAP substrate (Sigma 104) and the other daughter received 200 microliters/well betagal substrate (Sigma N-1127). Once developed, cell plates were read at 405 nM. SPAP data were normalized to beta-gal, and % maximum inhibition of transactivation was calculated relative to the 1 micromolar rosiglitazone positive control. Each of the above Examples 1–36 had >50% inhibition of transactivation by 100 nM rosiglitazone in this PPAR-gamma cell based reporter gene assay.

Adipocyte Differentiation Assay

C3H10T1/2 clone 8 murine fibroblasts (American Type Culture Collection) below passage 22 were maintained in Dulbecco's modified Eagle's medium (Life Technologies, Inc.) supplemented with 10% fetal calf serum and 100 units/mL penicillin G and 100 microgram/mL streptomycin. One day after passage into 96-well microtiter plates (12.5× 103 cells/cm$^2$), the cells were treated with 150 nM rosiglitazone plus 1 micromolar insulin and 1 micromolar 9-cis-retinoic acid (Sigma, St. Louis, Mo.). Vehicle or test compounds, which had been solublized to 10 mM in DMSO and then serially diluted from 1e-5 M to 1e-10 M into medium, were added. After 7 days, cells were lysed in 0.01% Digitonin (Sigma, St. Louis, Mo.) and the lipogenic activity determined by measuring total triglycerides using a Glycerol-Triglyceride (GPO-Trinder) kit (337-B,Sigma, St. Louis, Mo.). The mixture was incubated at 37° C. for 2 h and the absorbance read at 550 nm. The % maximum inhibition of lipogenesis was calculated relative to the vehicle treated cells. Each of the above Examples 1–36 had >50% inhibition of lipogenesis induced by 150 nM rosiglitazone in this adipocyte differentiation assay.

Osteoblast Differentiation Assay (Alkaline Phosphatase Activity)

C3H10T1/2 clone 8 murine fibroblasts (American Type Culture Collection) below passage 22 were maintained in Dulbecco's modified Eagle's medium (Life Technologies, Inc.) supplemented with 10% fetal calf serum and 100 units/mL penicillin G and 100 microgram/mL streptomycin. One day after passage into 96-well microtiter plates (12.5× 103 cells/cm$^2$), the cells were treated with 625 nanomolar all-trans retinoic acid, 1 micromolar rosiglitazone and 1 micromolar insulin (Sigma, St. Louis, Mo.). Vehicle or test compounds, which had been solublized to 10 mM in DMSO and then serially diluted from 2e-5 M to 4e-8 M into medium, were added. After 7 days, alkaline phosphatase activity, a surrogate measure for osteogenesis, was determined using Sigma-Fast pNPP substrate (N-2770) according to the manufacturer's specifications (Sigma, St. Louis, Mo.) (see Paulik, M. A. and Lenhard, J. M., Cell Tissue Res., (1997), Vol. 290, pp 79–87). The substrate (50 microliters/well) was incubated with the cells at 37° C. for 10 min and the absorbance read at 405 nm. The % maximum stimulation of alkaline phosphatase activity was calculated relative to cells treated with 10 micromolar all-trans retinoic acid.

| Compound | $pEC_{50}$ | % Stimulation |
| --- | --- | --- |
| Example 4 | 5.7 | 71 |

In Vivo Assay

Age and weight matched male C57BL/KsJ db/db mice (Jackson Labs, Bar Harbor, Me.) were housed 5 animals/cage at 72° F. and 50% relative humidity with a 12 h light and dark cycle, and fed chow diet (NIH R&M/Auto 6F-Ovals 5K67, PMI Feeds® Inc., Richmond, Ind.). Animals starting at 6 weeks of age were orally gavaged once daily (8:00–9:00 AM) with TPGS/PG (25/75) or 50 mg/kg the compound of Example 4 in TPGS/PG (25/75). After 2 weeks of dosing, the animals were anesthetized with isofluorane, blood was drawn by cardiac puncture, and non-fasting measurements of glucose, insulin, and glycosylated hemoglobin (GHB) were obtained. Blood glucose was determined using an automated chemistry analyzer (Technicon Axon). GHB measurements were performed using a Columnmate Analyzer (Helena Instrument). Insulin concentrations in serum were measured by chemiluminescence using an Origen Analyzer (Igen Inc.). Body weights were recorded at the beginning and end of the study. All data was calculated as the mean and standard error from experiments performed on $\geq 9$ animals per treatment group.

| Compound | Glucose (mmol/L) | Insulin (pmol/L) | GBH (%) | Body Weight Change (g) |
|---|---|---|---|---|
| Vehicle | 460 ± 40 | 6.1 ± 0.8 | 7.6 ± 0.4 | 0.9 ± 0.4 |
| Example 4 | 380 ± 30 | 3.3 ± 0.4 | 6.6 ± 0.3 | 1.1 ± 0.5 |

What is claimed is:

1. A compound of the following formula

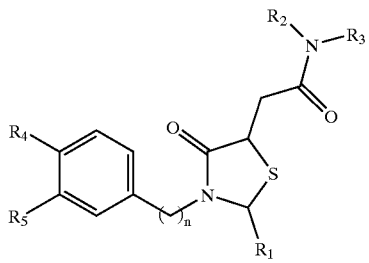

or a pharmaceutically acceptable salt or solvate thereof, where n is 2, 3, or 4, $R_1$ is hexyl, heptyl, or $C_{4-6}$alkyl-phenyl, $R_2$ is butyl or benzyl optionally substituted with 1 or 2 halogen, $R_3$ is butyl, benzyl optionally substituted with a trifluoromethyl group or with 1 to 3 halogen, —$C_4H_8$OH, p-pyridyl, o-pyridyl, ethylpropionate, propyl, ethyl acetate, o-thiophenmethyl, 2,3-methylenedioxobenzyl, 2-thiazolemethyl, 2-furfuryl, $R_4$ is —COOH, —NHC(O)$NH_2$, —NHS($CH_3$)$O_2$, —S($NH_2$)$O_2$, hydantoin, —OH, —$OCH_2CO_2H$, —$OCH_2CONH_2$, —$OCH_3$, $R_5$ is hydrogen or $R_5$ and $R_4$ are bonded together to form a methylenedioxo ring.

2. The compound of claim 1 wherein $R_3$ is butyl, benzyl optionally substituted with 1 or 2 halogen, or p-pyridyl.

3. A compound of claim 1 wherein the stereochemistry around the 2 and 5 carbon atoms is such that the compound is the trans pair of the (2S, 5S) enantiomer and the (2R, 5R) enantiomer.

4. A compound of claim 3 wherein the stereochemistry around the 2 and 5 carbon atoms is such that the compound is the (2S,5S) enantiomer.

5. The compound of claim 1 wherein said compound is selected from the group consisting of 4-(4-(4-carboxyphenyl)butyl)-2-heptyl-4-oxo-5-thiazolidine N,N-dibenzylacetamide, (2S*,5S*)-4-(4-(4-carboxyphenyl)butyl)-2-heptyl-4-oxo-5-thiazolidine N,N-dibenzylacetamide, (2S,5S)-4-(4-(4-carboxyphenyl)butyl)-2-heptyl-4-oxo-5-thiazolidine N,N-dibenzylacetamide, (2S*,5S*)-4-(4-(4-carboxyphenyl)butyl)-2-hexyl-4-oxo-5-thiazolidine N,N-dibutylacetamide, (2S*,5S*)-4-(2-(4-carboxyphenyl)ethyl)-2-octyl-4-oxo-5-thiazolidine N,N-dibenzylacetamide, (2R*,5S*)-4-(2-(4-carboxyphenyl)ethyl)-2-octyl-4-oxo-5-thiazolidine N,N-dibenzylacetamide, (2S*,5S*)-4-(2-(4-carboxyphenyl)ethyl)-2-octyl-4-oxo-5-thiazolidine N,N-di-(3-iodo)benzylacetamide, (2S*,5S*)-4-(3-(4-carboxyphenyl)propyl)-2-heptyl-4-oxo-5-thiazolidine N,N-benzylacetamide, (2S*,5S*)-4-(4-(4-carboxyphenyl)butyl)-2-heptyl-4-oxo-5-thiazolidine N,N-di-(3-benzylacetamide, (2S*,5S*)-4-(2-(4-carboxyphenyl)ethyl)-2-(6-phenylhexyl)-4-oxo-5-thiazolidine N,N-dibenzylacetamide, (2S*,5S*)-4-(4-(4-carboxyphenyl)butyl)-2-(6-phenylhexyl)-4-oxo-5-thiazolidine N,N-dibenzylacetamide, 4-(4-(4-carboxyphenyl)butyl)-2-(4-phenylbutyl)-4-oxo-5-thiazolidine N,N-dibenzylacetamide, (2S*,5S*)-4-(2-(4-ureidophenyl)ethyl)-2-octyl-4-oxo-5-thiazolidine N,N-dibenzylacetamide, (2S*,5S*)-4-(2-(4-methylsulfonamidophenyl)ethyl)-2-octyl-4-oxo-5-thiazolidine N,N-dibenzylacetamide, (2S*,5S*)-4-(2-(4-aminosulfonylphenyl)ethyl)-2-octyl-4-oxo-5-thiazolidine N,N-dibenzylacetamide, (2S*,5S*)-4-(4-(4-carboxyphenyl)butyl)-2-heptyl-4-oxo-5-thiazolidine N-benzyl-N-(4-trifluorobenzyl)acetamide, (2R,5S*)-4-(4-(4-carboxyphenyl)butyl)-2-heptyl-4-oxo-5-thiazolidine N-benzyl-N-(4-trifluorobenzyl)acetamide, (2S*,5S*)-4-(2-(4-(3-hydantoino)phenyl)ethyl)-2-octyl-4-oxo-5-thiazolidine N,N-dibenzylacetamide, (2S*,5S*)-4-(2-(3,4-dioxomethylenephenyl)ethyl)-2-heptyl-4-oxo-5-thiazolidine N,N-dibenzylacetamide, (2S*,5S*)-4-(4-(4-carboxyphenyl)butyl)-2-octyl-4-oxo-5-thiazolidine N-benzyl-N-(4-hydroxybutyl)acetamide, (2S*,5S*)-4-(2-(3,4-dioxomethylenephenyl)ethyl)-2-octyl-4-oxo-5-thiazolidine N,N-dibenzylacetamide, (2S*,5S*)-4-(4-(4-carboxyphenyl)butyl)-2-heptyl-4-oxo-5-thiazolidine N-benzyl-N-(4-pyridyl)acetamide, (2S*,5S*)-4-(4-(4-carboxyphenyl)butyl)-2-heptyl-4-oxo-5-thiazolidine N-benzyl-N-(2-pyridyl)acetamide, (2S*,5S*)-4-(4-(4-carboxyphenyl)butyl)-2-heptyl-4-oxo-5-thiazolidine N-benzyl-N-(2-ethoxycarboxyethyl)acetamide, (2S*,5S*)-4-(4-(4-carboxyphenyl)butyl)-2-heptyl-4-oxo-5-thiazolidine N-benzyl-N-butylacetamide, (2S*,5S*)-4-(4-(4-carboxyphenyl)butyl)-2-heptyl-4-oxo-5-thiazolidine N-benzyl-N-isopropylacetamide, (2S*,5S*)-4-(2-(4-hydroxyphenyl)ethyl)-2-heptyl-4-oxo-5-thiazolidine N,N-dibenzylacetamide, (2S*,5S*)-4-(4-(4-carboxyphenyl)butyl)-2-heptyl-4-oxo-5-thiazolidine N-benzyl-N-ethoxycarboxymethylacetamide, (2S*,5S*)-4-(4-(4-carboxyphenyl)butyl)-2-heptyl-4-oxo-5-thiazolidine N,N-di-(4-fluorobenzyl)acetamide, (2S*,5S*)-4-(2-(4-carboxymethoxyphenyl)ethyl)-2-heptyl-4-oxo-5-thiazolidine N,N-dibenzylacetamide, (2S*,5S*)-4-(2-(4-carboxyamidomethoxyphenyl)ethyl)-2-heptyl-4-oxo-5-thiazolidine N,N-dibenzylacetamide, (2S*,5S*)-4-(2-(4-methoxyphenyl)ethyl)-2-heptyl-4-oxo-5-thiazolidine N,N-dibenzylacetamide, (2S*,5S*)-4-(4-(4-carboxyphenyl)butyl)-2-heptyl-4-oxo-5-thiazolidine N-benzyl-N-(2-thienylmethyl)acetamide, (2S*,5S*)-4-(4-(4-carboxyphenyl)butyl)-2-heptyl-4-oxo-5-thiazolidine N-benzyl-N-(2,3-dioxomethylenebenzyl)acetamide, (2S*,5S*)-4-(4-(4-carboxyphenyl)butyl)-2-heptyl-4-oxo-5-thiazolidine N-benzyl-N-(2-thiazolemethyl)acetamide, (2S*,5S*)-4-(4-(4-carboxyphenyl)butyl)-2-heptyl-4-oxo-5-thiazolidine N-benzyl-N-(2-furfuryl)acetamide, and pharmaceutically acceptable salts and solvates thereof.

6. The compound of claim 5 wherein said compound is selected from the group consisting of (2S*,5S*)-4-(4-(4-carboxyphenyl)butyl)-2-heptyl-4-oxo-5-thiazolidine N,N-dibenzylacetamide, (2S,5S)-4-(4-(4-carboxyphenyl)butyl)-2-heptyl-4-oxo-5-thiazolidine N,N-dibenzylacetamide, (2S*,5S*)-4-(4-(4-carboxyphenyl)butyl)-2-hexyl-4-oxo-5-thiazolidine N,N-dibutylacetamide, (2S*,5S*)-4-(4-(4-carboxyphenyl)butyl)-2-octyl-4-oxo-5-thiazolidine N-benzyl-N-(4-hydroxybutyl)acetamide, (2S*,5S*)-4-(4-(4-carboxyphenyl)butyl)-2-heptyl-4-oxo-5-thiazolidine N-benzyl-N-(4-pyridyl)acetamide, (2S*,5S*)-4-(4-(4-carboxyphenyl)butyl)-2-heptyl-4-oxo-5-thiazolidine N-benzyl-N-(2-thiazolemethyl)acetamide, and pharmaceutically acceptable salts and solvates thereof.

7. A pharmaceutical composition comprising a compound according to claim 1.

8. A pharmaceutical composition according to claim 7 further comprising a pharmaceutically acceptable diluent or carrier.

9. A method for the prevention or treatment of osteoporosis comprising administration of a therapeutically effective amount of a compound of claim 1 to a patient in need thereof.

* * * * *